United States Patent
Ando et al.

(10) Patent No.: US 11,246,966 B2
(45) Date of Patent: Feb. 15, 2022

(54) COPOLYMER-COMPRISING ANTIMICROBIAL, CELL CULTURE, ANTITHROMBOTIC, OR BIOPHARMACEUTICAL ARTICLE

(71) Applicants: NATIONAL UNIVERSITY CORPORATION NARA INSTITUTE OF SCIENCE AND TECHNOLOGY, Ikoma (JP); DAIKIN INDUSTRIES, LTD., Osaka (JP)

(72) Inventors: Tsuyoshi Ando, Ikoma (JP); Masayasu Totani, Ikoma (JP); Masao Tanihara, Ikoma (JP); Shota Shibutani, Osaka (JP); Yoshito Tanaka, Osaka (JP); Takuma Kawabe, Osaka (JP); Haruhiko Mohri, Osaka (JP)

(73) Assignees: NATIONAL UNIVERSITY CORPORATION NARA INSTITUTE OF SCIENCE AND TECHNOLOGY, Ikoma (JP); DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/639,271

(22) PCT Filed: Aug. 2, 2018

(86) PCT No.: PCT/JP2018/029012
§ 371 (c)(1),
(2) Date: Feb. 14, 2020

(87) PCT Pub. No.: WO2019/035365
PCT Pub. Date: Feb. 21, 2019

(65) Prior Publication Data
US 2020/0246512 A1 Aug. 6, 2020

(30) Foreign Application Priority Data

Aug. 15, 2007 (JP) .............................. JP2017-156904

(51) Int. Cl.
| | |
|---|---|
| A61L 33/06 | (2006.01) |
| A61L 27/16 | (2006.01) |
| A61L 27/54 | (2006.01) |
| A61L 29/04 | (2006.01) |
| A61L 29/16 | (2006.01) |
| A61L 31/04 | (2006.01) |
| A61L 31/16 | (2006.01) |
| C08L 23/20 | (2006.01) |
| C08L 29/04 | (2006.01) |
| C08L 31/04 | (2006.01) |
| C12M 3/00 | (2006.01) |

(52) U.S. Cl.
CPC ............. *A61L 33/064* (2013.01); *A61L 27/16* (2013.01); *A61L 27/54* (2013.01); *A61L 29/041* (2013.01); *A61L 29/16* (2013.01); *A61L 31/04* (2013.01); *A61L 31/16* (2013.01); *C08L 23/20* (2013.01); *C08L 29/04* (2013.01); *C08L 31/04* (2013.01); *C12M 3/00* (2013.01)

(58) Field of Classification Search
None
See application file for complete search history.

(56) References Cited

U.S. PATENT DOCUMENTS 5,658,625 A * 8/1997 Bradfute ................. B32B 27/08
428/34.9

FOREIGN PATENT DOCUMENTS

| EP | 0 534 014 A1 | 3/1993 |
| JP | 63-85198 A | 4/1988 |
| JP | 2016-026520 A | 2/2016 |

OTHER PUBLICATIONS

Borkar et al., "Controlled Copolymerization of Vinyl Acetate with 1-Alkenes and Their Fluoro Derivatives by Degenerative Transfer", Journal of Polymer Science: Part A: Polymer Chemistry, 43, 2005, pp. 3728-3736. (Year: 2005).*
International Preliminary Report on Patentability dated Feb. 18, 2020 with Written Opinion in International Application No. PCT/JP2018/029012.
International Search Report for PCT/JP2018/029012 dated Nov. 6, 2018 [PCT/ISA/210].
Extended European Search Report dated Aug. 18, 2021 in European Application No. 18845662.8.

* cited by examiner

*Primary Examiner* — Melissa L Fisher
(74) *Attorney, Agent, or Firm* — Sughrue Mion, PLLC

(57) ABSTRACT

An antimicrobial article, a cell culture article, an antithrombotic article, or a biopharmaceutical article that can reduce adhesion of proteins, blood components, cells, or bacteria containing a copolymer that contains a polymerized unit (A) represented by —$CH_2$—CHOH— and a polymerized unit (B) represented by —$CH_2$—$CX_2$—, wherein Xs are the same as or different from each other, and are each an alkyl group having a linear, branched, or cyclic structure, and optionally containing an oxygen atom between carbon atoms, an alkoxy group having a linear, branched, or cyclic structure, and optionally containing a hetero atom between carbon atoms, a siloxy group having a carbon number of 3 or greater, an ester group containing an aromatic ring or an alkyl group and having a linear, branched, or cyclic structure, or H, excluding those in which both Xs are H.

4 Claims, No Drawings

COPOLYMER-COMPRISING ANTIMICROBIAL, CELL CULTURE, ANTITHROMBOTIC, OR BIOPHARMACEUTICAL ARTICLE

CROSS REFERENCE TO RELATED APPLICATIONS

This application is a National Stage of International Application No. PCT/JP2018/029012 filed Aug. 2, 2018, claiming priority based on Japanese Patent Application No. 2017-156904 filed Aug. 15, 2017.

TECHNICAL FIELD

The invention relates to antimicrobial articles, cell culture articles, antithrombotic articles, or biopharmaceutical articles.

BACKGROUND ART

Artificial materials in contact with biological components may suffer adhesion of components such as proteins or platelets on their surfaces, resulting in disadvantages such as poor performance of the materials and harmful influences on biological reactions. This creates a strong demand for artificial materials with biocompatible surfaces to be used in applications involving contact with biological components.

Patent Literature 1 discloses a compound for preventing protein adhesion. This compound is for forming a coating layer that prevents adsorption of proteins on the surface of an article, and is formed from a fluorine-containing polymer.

CITATION LIST

Patent Literature

Patent Literature 1: JP 2016-026520 A

SUMMARY OF INVENTION

Technical Problem

The invention aims to provide an antimicrobial article, a cell culture article, an antithrombotic article, or a biopharmaceutical article that can reduce adhesion of proteins, blood components, cells, or bacteria.

Solution to Problem

The inventors examined solutions to the above technical problem and found that a copolymer containing a vinyl alcohol unit and a vinyl monomer unit having a side chain can exhibit low protein adhesion, low cell adhesion, antithrombotic performance, and antimicrobial performance, thereby completing the invention.

In other words, the invention relates to an antimicrobial article, a cell culture article, an antithrombotic article, or a biopharmaceutical article containing a copolymer, the copolymer containing: a polymerized unit (A) represented by —$CH_2$—CHOH—; and a polymerized unit (B) represented by —$CH_2$—$CX_2$—, wherein Xs are the same as or different from each other, and are each an alkyl group having a carbon number of 1 or greater, having a linear, branched, or cyclic structure, and optionally containing an oxygen atom between carbon atoms, an alkoxy group having a carbon number of 1 or greater, having a linear, branched, or cyclic structure, and optionally containing a hetero atom between carbon atoms, a siloxy group having a carbon number of 3 or greater, an ester group containing an aromatic ring or an alkyl group having a carbon number of 1 or greater and having a linear, branched, or cyclic structure, or H, excluding those in which both Xs are H.

In the copolymer, the alkyl group preferably has a carbon number of 1 to 17, the alkoxy group preferably has a carbon number of 3 to 19, more preferably 3 to 18, the siloxy group preferably has a carbon number of 3 to 18, and the ester group preferably has a carbon number of 1 to 19, more preferably 1 to 17.

In the copolymer, the polymerized unit (A) and the polymerized unit (B) preferably give a mole ratio (A/B) of 5/95 to 95/5.

The invention also relates to a copolymer containing: a polymerized unit (A) represented by —$CH_2$—CHOH—; and a polymerized unit (B-1) represented by —$CH_2$—$CX_2$—, wherein Xs are the same as or different from each other, and are each an alkyl group having a carbon number of 1 or greater, having a linear, branched, or cyclic structure, and optionally containing an oxygen atom between carbon atoms.

Advantageous Effects of Invention

The article of the invention can reduce adhesion of proteins, blood components, cells, or bacteria.

DESCRIPTION OF EMBODIMENTS

The invention will be specifically described hereinbelow.

The article of the invention contains a copolymer that contains a polymerized unit (A) and a polymerized unit (B).

The polymerized unit (A) is a polymerized unit represented by —$CH_2$—CHOH— and based on vinyl alcohol.

The polymerized unit (B) is represented by —$CH_2$—$CX_2$—, wherein Xs are the same as or different from each other, and are each an alkyl group having a carbon number of 1 or greater, having a linear, branched, or cyclic structure, and optionally containing an oxygen atom between carbon atoms, an alkoxy group having a carbon number of 1 or greater, having a linear, branched, or cyclic structure, and optionally containing a hetero atom between carbon atoms, a siloxy group having a carbon number of 3 or greater, an ester group containing an aromatic ring or an alkyl group having a carbon number of 1 or greater and having a linear, branched, or cyclic structure, or H, excluding those in which both Xs are H.

The alkyl group and the alkoxy group are each preferably free from a fluorine atom.

The hetero atom is preferably a hetero atom having a valence of 2 or higher, more preferably an oxygen atom, a nitrogen atom, or a sulfur atom, still more preferably an oxygen atom.

In order to further reduce the adhesion of proteins, blood components, cells, or bacteria, the alkyl group preferably has a carbon number of 1 to 17, more preferably 3 to 14.

The carbon number is preferably 3 or greater, and also preferably 4 or greater.

The carbon number is preferably 14 or smaller, may be 11 or smaller, and may be 9 or smaller.

Preferred specific examples of the alkyl group include —$CH_3$, —$CH_2CH_3$, —$CH_2CH_2CH_3$, and —$CH_2CH_2CH_2CH_3$.

Both Xs are also preferably alkyl groups. A copolymer in which both Xs are alkyl groups has excellent film strength and heat resistance.

When both Xs are alkyl groups, one of them is preferably —CH$_3$.

In order to further reduce the adhesion of proteins, blood components, cells, or bacteria, the carbon number of the alkoxy group is preferably 3 to 18, more preferably 3 to 12, still more preferably 4 to 10, particularly preferably 5 to 8.

In order to further reduce the adhesion of proteins, blood components, cells, or bacteria, the carbon number of the siloxy group is preferably 3 to 18, more preferably 3 to 16.

The siloxy group is preferably a group represented by the following formula:

—O—SiR$^1$R$^2$R$^3$ wherein R$^1$, R$^2$, and R$^3$ are the same as or different from each other, and are each a C1-C8 alkyl group or a phenyl group.

Specific examples of the siloxy group preferably include at least one selected from the group consisting of —O—Si (Me)$_3$, —O—Si(Et)$_3$, —O—Si(Me)$_2$(tBu), —O—Si(iPr)$_3$, and —O—Si(Ph)$_2$(tBu), more preferably include at least one selected from the group consisting of —O—Si(Me)$_3$ and —O—Si(Et)$_3$.

In the present description, Me represents a methyl group, Et represents an ethyl group, tBu represents a tert-butyl group, iPr represents an isopropyl group, and Ph represents a phenyl group.

Examples of the ester group include groups represented by —O(C=O)R (wherein R is a C1-C17 hydrocarbon group). R in the formula is preferably a C1-C11 alkyl group, more preferably a C1-C5 alkyl group, particularly preferably a C1-C3 alkyl group.

In order to further reduce the adhesion of proteins, blood components, cells, or bacteria, at least one of the two Xs is preferably a group represented by the formula: —(CH$_2$)$_n$CH$_3$ (wherein n is an integer of 0 to 16), a C3-C18 siloxy group, an ester group represented by —O(C=O)R (wherein R is a C1-C19 hydrocarbon group), or an alkoxy group represented by the formula: —O—Y (wherein Y is a C3-C18 linear alkyl group, a C3-C11 branched alkyl group, a C5-C10 alkyl group having a cyclic structure, a group represented by the formula (A): —(CH$_2$—O)$_m$—R$^4$ (wherein R$^4$ is a C1-C2 alkyl group, and m is an integer of 1 to 5), a C4-C12 cycloalkyl group containing a hetero atom, or a C7-C19 alkyl group containing an aromatic ring).

Y is also preferably a C4-C18 linear alkyl group, a C4-C11 branched alkyl group, a group represented by the formula (A): —(CH$_2$—O)$_m$—R$^4$ (wherein R$^4$ is a C1-C2 alkyl group, and m is an integer of 1 to 5), or a C7-C18 alkyl group containing an aromatic ring.

In particular, at least one of the two Xs is preferably —(CH$_2$)$_n$CH$_3$ (wherein n is an integer of 0 to 16), —O(C=O) CH$_3$, —OCH$_2$CH(CH$_2$CH$_3$) CH$_2$CH$_2$CH$_2$CH$_3$, or —OC(CH$_3$)$_3$. The above n is more preferably 0 to 10, still more preferably 0 to 8, particularly preferably 0 to 6. The lower limit of n may be 2 or may be 3.

Specific examples of the group represented by —(CH$_2$)$_n$CH$_3$ (wherein n is an integer of 0 to 16) include —CH$_3$, —(CH$_2$)$_2$CH$_3$, —(CH$_2$)$_3$CH$_3$, and —(CH$_2$)$_4$CH$_3$.

When one of the two Xs is any of the above groups, the other is preferably H.

When both Xs are alkyl groups, one of them is preferably —CH$_3$.

R is preferably a C1-C19 hydrocarbon group, more preferably a C1-C17 hydrocarbon group.

The hydrocarbon group is preferably a C1-C17 linear alkyl group, a C3-C11 branched alkyl group, a C5-C10 alkyl group having a cyclic structure, a phenyl group, or a C7-C19 alkyl group containing an aromatic ring. The C1-C17 linear alkyl group for R is preferably a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, or an n-heptadecyl group. Preferred among these are a methyl group and an ethyl group.

The C3-C11 branched alkyl group is preferably an isopropyl group, a sec-butyl group, a tert-butyl group, an isobutyl group, an isoamyl group, an isohexyl group, an isoheptyl group, an isooctyl group, a 1,2-dimethylpropyl group, a 1,1-methylethylpropyl group, a 1,1-diethylpropyl group, a 1,3-dimethylbutyl group, a 2-ethylbutyl group, a 2-ethylhexyl group, a 2-methyloctyl group, a 1-pentylhexyl group, a 1-methylheptyl group, or a 4-ethyl-1-methyloctyl group.

The C5-C10 alkyl group having a cyclic structure is preferably a cyclopentyl group, a cyclohexyl group, a cyclopentyl group, a cyclooctyl group, a cyclononyl group, a cyclodecanyl group, a 2-methylcyclopentyl group, a 3-methylcyclopentyl group, a 2-ethylcyclopentyl group, a 3-ethylcyclopentyl group, a 2-methylcyclohexyl group, a 3-methylcyclohexyl group, a 4-methylcyclohexyl group, a 2-ethylcyclohexyl group, a 3-ethylcyclohexyl group, a 4-ethylcyclohexyl group, a cyclohexylmethyl group, or a 2-cyclohexylethyl group.

The C7-C19 alkyl group containing an aromatic ring is preferably —CH$_2$-Ph, —C(Ph)$_3$, a group represented by the following formula:

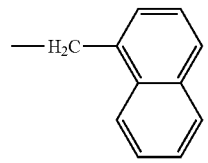

[Chem. 1]

or a group represented by the following formula:

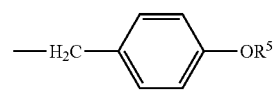

[Chem. 2]

wherein R$^5$ is Me or Et.

The C3-C18 linear alkyl group for Y is preferably an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, or an n-octadecyl group.

The C3-C11 branched alkyl group for Y is preferably an isopropyl group, a sec-butyl group, a tert-butyl group, an isobutyl group, an isoamyl group, an isohexyl group, an isoheptyl group, an isooctyl group, a 1,2-dimethylpropyl group, a 1,1-methylethylpropyl group, a 1,1-diethylpropyl group, a 1,3-dimethylbutyl group, a 2-ethylbutyl group, a 2-ethylhexyl group, a 2-methyloctyl group, a 1-pentylhexyl group, a 1-methylheptyl group, or a 4-ethyl-1-methyloctyl group.

The C5-C10 alkyl group having a cyclic structure for Y is preferably a cyclopentyl group, a cyclohexyl group, a cyclopentyl group, a cyclooctyl group, a cyclononyl group, a cyclodecanyl group, a 2-methylcyclopentyl group, a 3-methylcyclopentyl group, a 2-ethylcyclopentyl group, a 3-ethylcyclopentyl group, a 2-methylcyclohexyl group, a 3-methylcyclohexyl group, a 4-methylcyclohexyl group, a 2-ethylcyclohexyl group, a 3-ethylcyclohexyl group, a 4-ethylcyclohexyl group, a cyclohexylmethyl group, or a 2-cyclohexylethyl group.

The group represented by the formula (A): $-(CH_2-O)_m-R^4$ for Y is preferably a group derived from 2-methoxyethyl vinyl ether, 2-ethoxyethyl vinyl ether, 3-methoxypropyl vinyl ether, 3-ethoxypropyl vinyl ether, 3-ethoxybutyl vinyl ether, methyl diethylene glycol vinyl ether, ethyl diethylene glycol vinyl ether, methyl triethylene glycol vinyl ether, methyl tetraethylene glycol vinyl ether, or methyl pentaethylene glycol vinyl ether. In other words, the group represented by the formula (A) preferably has a structure formed by removing the $CH_2=CH-O-$ structure from the vinyl ether.

An example of the C4-C12 cycloalkyl group containing a hetero atom for Y is a group represented by the following formula.

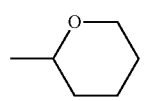

[Chem. 3]

The C7-C19 alkyl group containing an aromatic ring for Y is preferably $-CH_2-Ph$, $-C(Ph)_3$, a group represented by the following formula:

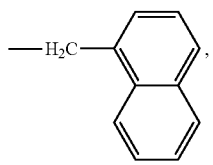

[Chem. 4]

or a group represented by the following formula:

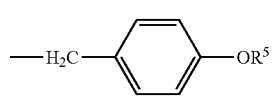

[Chem. 5]

wherein $R^5$ is Me or Et.

In particular, in cases of attaching importance to low adhesion of proteins, at least one of the two Xs is preferably a group represented by the formula: $-(CH_2)_nCH_3$ (wherein n is an integer of 0 to 16), $-O(CO)CH_3$, or an alkoxy group represented by the formula: $-O-Y$ (wherein Y is a C3-C18 linear alkyl group, a C3-C11 branched alkyl group, a C5-C10 alkyl group having a cyclic structure, a group represented by the formula (A): $-(CH_2-O)_m-R^4$ (wherein $R^4$ is a C1-C2 alkyl group, and m is an integer of 1 to 5), a C4-C12 cycloalkyl group containing a hetero atom, or a C7-C19 alkyl group containing an aromatic ring).

Also, at least one of the two Xs is preferably a group represented by the formula: $-(CH_2)_nCH_3$ (wherein n is an integer of 0 to 16), $-O(CO)CH_3$, or an alkoxy group represented by the formula: $-O-Y$ (wherein Y is a C4-C18 linear alkyl group, a C4-C11 branched alkyl group, a group represented by the formula (A): $-(CH_2-O)_m-R^4$ (wherein $R^4$ is a C1-C2 alkyl group, and m is an integer of 1 to 5), or a C7-C18 alkyl group containing an aromatic ring). The C3-C18 linear alkyl group for Y is preferably an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, or an n-octadecyl group.

The C3-C11 branched alkyl group for Y is preferably an isopropyl group, a sec-butyl group, a tert-butyl group, an isobutyl group, an isoamyl group, an isohexyl group, an isoheptyl group, an isooctyl group, a 1,2-dimethylpropyl group, a 1,1-methylethylpropyl group, a 1,1-diethylpropyl group, a 1,3-dimethylbutyl group, a 2-ethylbutyl group, a 2-ethylhexyl group, a 2-methyloctyl group, a 1-pentylhexyl group, a 1-methylheptyl group, or a 4-ethyl-1-methyloctyl group.

The C5-C10 alkyl group having a cyclic structure for Y is preferably a cyclopentyl group, a cyclohexyl group, a cyclopentyl group, a cyclooctyl group, a cyclononyl group, a cyclodecanyl group, a 2-methylcyclopentyl group, a 3-methylcyclopentyl group, a 2-ethylcyclopentyl group, a 3-ethylcyclopentyl group, a 2-methylcyclohexyl group, a 3-methylcyclohexyl group, a 4-methylcyclohexyl group, a 2-ethylcyclohexyl group, a 3-ethylcyclohexyl group, a 4-ethylcyclohexyl group, a cyclohexylmethyl group, or a 2-cyclohexylethyl group.

The group represented by the formula (A): $-(CH_2-O)_m-R^4$ for Y is preferably a group derived from 2-methoxyethyl vinyl ether, 2-ethoxyethyl vinyl ether, 3-methoxypropyl vinyl ether, 3-ethoxypropyl vinyl ether, 3-ethoxybutyl vinyl ether, methyl diethylene glycol vinyl ether, ethyl diethylene glycol vinyl ether, methyl triethylene glycol vinyl ether, methyl tetraethylene glycol vinyl ether, or methyl pentaethylene glycol vinyl ether. In other words, the group represented by the formula (A) preferably has a structure formed by removing the $CH_2=CH-O-$ structure from the vinyl ether.

An example of the C4-C12 cycloalkyl group containing a hetero atom for Y is a group represented by the following formula.

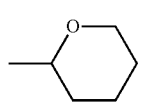

[Chem. 6]

The C7-C18 alkyl group containing an aromatic ring for Y is preferably $-CH_2-Ph$, $-C(Ph)_3$, a group represented by the following formula:

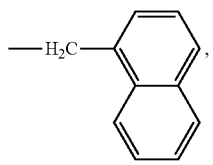

or a group represented by the following formula:

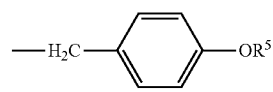

wherein $R^5$ is Me or Et.

In particular, at least one of the two Xs is preferably —$(CH_2)_nCH_3$ (wherein n is an integer of 0 to 16), —$O(CO)CH_3$, —$OCH_2CH(CH_2CH_3)$ $CH_2CH_2CH_2CH_3$, or —$OC(CH_3)_3$. The above n is more preferably 0 to 10, still more preferably 0 to 8. The lower limit of n may be 3.

Specific examples of the group represented by —$(CH_2)_nCH_3$ (wherein n is an integer of 0 to 16) include —$CH_3$, —$CH_2CH_3$, —$(CH_2)_2CH_3$, —$(CH_2)_3CH_3$, and —$(CH_2)_4CH_3$.

When one of the two Xs is any of the above groups, the other may be H.

When both Xs are alkyl groups, one of them is preferably —$CH_3$.

When the Xs are these groups, the article is preferably the cell culture article or the biopharmaceutical article.

In particular, in cases of attaching importance to low adhesion of blood components, at least one of the two Xs is preferably a group represented by the formula: —$(CH_2)_nCH_3$ (wherein n is an integer of 0 to 16), —$O(CO)CH_3$, or an alkoxy group represented by the formula: —O—Y (wherein Y is a C3-C18 linear alkyl group, a C3-C11 branched alkyl group, a C5-C10 alkyl group having a cyclic structure, a group represented by the formula (A): —$(CH_2$—$O)_m$—$R^4$ (wherein $R^4$ is a C1-C2 alkyl group, and m is an integer of 1 to 5), a C4-C12 cycloalkyl group containing a hetero atom, or a C7-C19 alkyl group containing an aromatic ring).

Also, at least one of the two Xs is preferably a group represented by the formula: —$(CH_2)_nCH_3$ (wherein n is an integer of 0 to 16), —$O(CO)CH_3$, or an alkoxy group represented by the formula: —O—Y (wherein Y is a C4-C18 linear alkyl group, a C4-C11 branched alkyl group, a group represented by the formula (A): —$(CH_2$—$O)_m$—$R^4$ (wherein $R^4$ is a C1-C2 alkyl group, and m is an integer of 1 to 5), or a C7-C18 alkyl group containing an aromatic ring).

The C3-C18 linear alkyl group for Y is preferably an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, or an n-octadecyl group.

The C3-C11 branched alkyl group for Y is preferably an isopropyl group, a sec-butyl group, a tert-butyl group, an isobutyl group, an isoamyl group, an isohexyl group, an isoheptyl group, an isooctyl group, a 1,2-dimethylpropyl group, a 1,1-methylethylpropyl group, a 1,1-diethylpropyl group, a 1,3-dimethylbutyl group, a 2-ethylbutyl group, a 2-ethylhexyl group, a 2-methyloctyl group, a 1-pentylhexyl group, a 1-methylheptyl group, or a 4-ethyl-1-methyloctyl group.

The C5-C10 alkyl group having a cyclic structure for Y is preferably a cyclopentyl group, a cyclohexyl group, a cyclopentyl group, a cyclooctyl group, a cyclononyl group, a cyclodecanyl group, a 2-methylcyclopentyl group, a 3-methylcyclopentyl group, a 2-ethylcyclopentyl group, a 3-ethylcyclopentyl group, a 2-methylcyclohexyl group, a 3-methylcyclohexyl group, a 4-methylcyclohexyl group, a 2-ethylcyclohexyl group, a 3-ethylcyclohexyl group, a 4-ethylcyclohexyl group, a cyclohexylmethyl group, or 2-cyclohexylethyl group.

The group represented by the formula (A): —$(CH_2$—$O)_m$—$R^4$ for Y is preferably a group derived from 2-methoxyethyl vinyl ether, 2-ethoxyethyl vinyl ether, 3-methoxypropyl vinyl ether, 3-ethoxypropyl vinyl ether, 3-ethoxybutyl vinyl ether, methyl diethylene glycol vinyl ether, ethyl diethylene glycol vinyl ether, methyl triethylene glycol vinyl ether, methyl tetraethylene glycol vinyl ether, or methyl pentaethylene glycol vinyl ether. In other words, the group represented by the formula (A) preferably has a structure formed by removing the $CH_2$=CH—O— structure from the vinyl ether.

An example of the C4-C12 cycloalkyl group containing a hetero atom for Y is a group represented by the following formula.

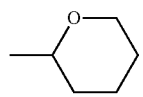

The C7-C18 alkyl group containing an aromatic ring for Y is preferably —$CH_2$-Ph, —$C(Ph)_3$, a group represented by the following formula:

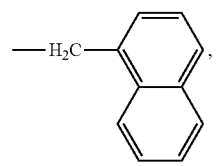

or a group represented by the following formula:

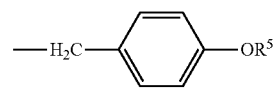

wherein $R^5$ is Me or Et.

In particular, at least one of the two Xs is preferably —$(CH_2)_nCH_3$ (wherein n is an integer of 0 to 16), —$O(CO)CH_3$, —$OCH_2CH(CH_2CH_3)$ $CH_2CH_2CH_2CH_3$, or —$OC(CH_3)_3$. The above n is more preferably 0 to 10, still more preferably 0 to 8. The lower limit of n may be 3.

Specific examples of the group represented by —$(CH_2)_nCH_3$ (wherein n is an integer of 0 to 16) include —$CH_3$, —$CH_2CH_3$, —$(CH_2)_2CH_3$, —$(CH_2)_3CH_3$, and —$(CH_2)_4CH_3$.

When one of the two Xs is any of the above groups, the other may be H.

When both Xs are alkyl groups, one of them is preferably —CH₃. When the Xs are these groups, the article is preferably the antithrombotic article.

In particular, in cases of attaching importance to low adhesion of cells, at least one of the two Xs is preferably a group represented by the formula: —(CH₂)ₙCH₃ (wherein n is an integer of 0 to 16), —O(CO)CH₃, or an alkoxy group represented by the formula: —O—Y (wherein Y is a C3-C18 linear alkyl group, a C3-C11 branched alkyl group, a C5-C10 alkyl group having a cyclic structure, a group represented by the formula (A): —(CH₂—O)ₘ—R⁴ (wherein R⁴ is a C1-C2 alkyl group, and m is an integer of 1 to 5), a C4-C12 cycloalkyl group containing a hetero atom, or a C7-C19 alkyl group containing an aromatic ring).

Also, at least one of the two Xs is preferably a group represented by the formula: —(CH₂)ₙCH₃ (wherein n is an integer of 0 to 16), —O(CO)CH₃, or an alkoxy group represented by the formula: —O—Y (wherein Y is a C4-C18 linear alkyl group, a C4-C11 branched alkyl group, a group represented by the formula (A): —(CH₂—O)ₘ—R⁴ (wherein R⁴ is a C1-C2 alkyl group, and m is an integer of 1 to 5), or a C7-C18 alkyl group containing an aromatic ring).

The C3-C18 linear alkyl group for Y is preferably an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, or an n-octadecyl group.

The C3-C11 branched alkyl group for Y is preferably an isopropyl group, a sec-butyl group, a tert-butyl group, an isobutyl group, an isoamyl group, an isohexyl group, an isoheptyl group, an isooctyl group, a 1,2-dimethylpropyl group, a 1,1-methylethylpropyl group, a 1,1-diethylpropyl group, a 1,3-dimethylbutyl group, a 2-ethylbutyl group, a 2-ethylhexyl group, a 2-methyloctyl group, a 1-pentylhexyl group, a 1-methylheptyl group, or a 4-ethyl-1-methyloctyl group.

The C5-C10 alkyl group having a cyclic structure for Y is preferably a cyclopentyl group, a cyclohexyl group, a cyclopentyl group, a cyclooctyl group, a cyclononyl group, a cyclodecanyl group, a 2-methylcyclopentyl group, a 3-methylcyclopentyl group, a 2-ethylcyclopentyl group, a 3-ethylcyclopentyl group, a 2-methylcyclohexyl group, a 3-methylcyclohexyl group, a 4-methylcyclohexyl group, a 2-ethylcyclohexyl group, a 3-ethylcyclohexyl group, a 4-ethylcyclohexyl group, a cyclohexylmethyl group, or a 2-cyclohexylethyl group.

The group represented by the formula (A): —(CH₂—O)ₘ—R⁴ for Y is preferably a group derived from 2-methoxyethyl vinyl ether, 2-ethoxyethyl vinyl ether, 3-methoxypropyl vinyl ether, 3-ethoxypropyl vinyl ether, 3-ethoxybutyl vinyl ether, methyl diethylene glycol vinyl ether, ethyl diethylene glycol vinyl ether, methyl triethylene glycol vinyl ether, methyl tetraethylene glycol vinyl ether, or methyl pentaethylene glycol vinyl ether. In other words, the group represented by the formula (A) preferably has a structure formed by removing the CH₂=CH—O— structure from the vinyl ether.

An example of the C4-C12 cycloalkyl group containing a hetero atom for Y is a group represented by the following formula.

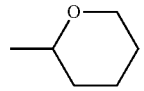
[Chem. 12]

The C7-C18 alkyl group containing an aromatic ring for Y is preferably —CH₂-Ph, —C(Ph)₃, a group represented by the following formula:

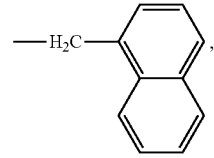
[Chem. 13]

or a group represented by the following formula:

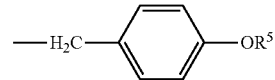
[Chem. 14]

wherein R⁵ is Me or Et.

In particular, at least one of the two Xs is preferably —(CH₂)ₙCH₃ (wherein n is an integer of 0 to 16), —O(CO)CH₃, —OCH₂CH(CH₂CH₃) CH₂CH₂CH₂CH₃, or —OC(CH₃)₃. The above n is more preferably 0 to 10, still more preferably 0 to 8. The lower limit of n may be 3.

Specific examples of the group represented by —(CH₂)ₙCH₃ (wherein n is an integer of 0 to 16) include —CH₃, —CH₂CH₃, —(CH₂)₂CH₃, —(CH₂)₃CH₃, and —(CH₂)₄CH₃.

When one of the two Xs is any of the above groups, the other may be H. When both Xs are alkyl groups, one of them is preferably —CH₃.

When the Xs are these groups, the article is preferably the cell culture article.

In particular, in cases of attaching importance to low adhesion of bacteria, at least one of the two Xs is preferably a group represented by the formula: —(CH₂)ₙCH₃ (wherein n is an integer of 0 to 16), —O(CO)CH₃, or an alkoxy group represented by the formula: —O—Y (wherein Y is a C3-C18 linear alkyl group, a C3-C11 branched alkyl group, a C5-C10 alkyl group having a cyclic structure, a group represented by the formula (A): —(CH₂—O)ₘ—R⁴ (wherein R⁴ is a C1-C2 alkyl group, and m is an integer of 1 to 5), a C4-C12 cycloalkyl group containing a hetero atom, or a C7-C19 alkyl group containing an aromatic ring).

Also, at least one of the two Xs is preferably a group represented by the formula: —(CH₂)ₙCH₃ (wherein n is an integer of 0 to 16), —O(CO)CH₃, or an alkoxy group represented by the formula: —O—Y (wherein Y is a C4-C18 linear alkyl group, a C4-C11 branched alkyl group, a group represented by the formula (A): —(CH₂—O)ₘ—R⁴ (wherein R⁴ is a C1-C2 alkyl group, and m is an integer of 1 to 5), or a C7-C18 alkyl group containing an aromatic ring).

The C3-C18 linear alkyl group for Y is preferably an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, or an n-octadecyl group.

The C3-C11 branched alkyl group for Y is preferably an isopropyl group, a sec-butyl group, a tert-butyl group, an isobutyl group, an isoamyl group, an isohexyl group, an isoheptyl group, an isooctyl group, a 1,2-dimethylpropyl group, a 1,1-methylethylpropyl group, a 1,1-diethylpropyl group, a 1,3-dimethylbutyl group, a 2-ethylbutyl group, a 2-ethylhexyl group, a 2-methyloctyl group, a 1-pentylhexyl group, a 1-methylheptyl group, or a 4-ethyl-1-methyloctyl group.

The C5-C10 alkyl group having a cyclic structure for Y is preferably a cyclopentyl group, a cyclohexyl group, a cyclopentyl group, a cyclooctyl group, a cyclononyl group, a cyclodecanyl group, a 2-methylcyclopentyl group, a 3-methylcyclopentyl group, a 2-ethylcyclopentyl group, a 3-ethylcyclopentyl group, a 2-methylcyclohexyl group, a 3-methylcyclohexyl group, a 4-methylcyclohexyl group, a 2-ethylcyclohexyl group, a 3-ethylcyclohexyl group, a 4-ethylcyclohexyl group, a cyclohexylmethyl group, or 2-cyclohexylethyl group.

The group represented by the formula (A): —(CH$_2$—O)$_m$—R$^4$ for Y is preferably a group derived from 2-methoxyethyl vinyl ether, 2-ethoxyethyl vinyl ether, 3-methoxypropyl vinyl ether, 3-ethoxypropyl vinyl ether, 3-ethoxybutyl vinyl ether, methyl diethylene glycol vinyl ether, ethyl diethylene glycol vinyl ether, methyl triethylene glycol vinyl ether, methyl tetraethylene glycol vinyl ether, or methyl pentaethylene glycol vinyl ether. In other words, the group represented by the formula (A) preferably has a structure formed by removing the CH$_2$=CH—O— structure from the vinyl ether.

An example of the C4-C12 cycloalkyl group containing a hetero atom for Y is a group represented by the following formula.

[Chem. 15]

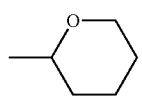

The C7-C18 alkyl group containing an aromatic ring for Y is preferably —CH$_2$-Ph, —C(Ph)$_3$, a group represented by the following formula:

[Chem. 16]

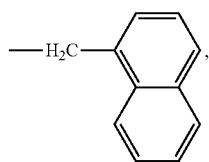

or a group represented by the following formula:

[Chem. 17]

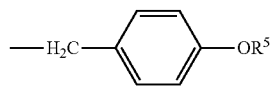

wherein R$^5$ is Me or Et.

In particular, at least one of the two Xs is preferably —(CH$_2$)$_n$CH$_3$ (wherein n is an integer of 0 to 16), —O(CO)CH$_3$, —OCH$_2$CH(CH$_2$CH$_3$) CH$_2$CH$_2$CH$_2$CH$_3$, or —OC(CH$_3$)$_3$. The above n is more preferably 0 to 10, still more preferably 0 to 8. The lower limit of n may be 3.

Specific examples of the group represented by —(CH$_2$)$_n$CH$_3$ (wherein n is an integer of 0 to 16) include —CH$_3$, —CH$_2$CH$_3$, —(CH$_2$)$_2$CH$_3$, —(CH$_2$)$_3$CH$_3$, and —(CH$_2$)$_4$CH$_3$.

When one of the two Xs is any of the above groups, the other may be H. When both Xs are alkyl groups, one of them is preferably —CH$_3$.

When the Xs are these groups, the article is preferably the antimicrobial article.

In the polymerized unit (B), one of the two Xs may be H and the other may be an alkyl group having a carbon number of 1 or greater, having a linear, branched, or cyclic structure, and optionally containing an oxygen atom between carbon atoms, an alkoxy group having a carbon number of 1 or greater, having a linear, branched, or cyclic structure, and optionally containing a hetero atom between carbon atoms, a siloxy group having a carbon number of 3 or greater, or an ester group containing an aromatic ring or an alkyl group having a carbon number of 1 or greater and having a linear, branched, or cyclic structure.

In order to further reduce the adhesion of proteins, blood components, cells, or bacteria, the polymerized unit (A) and the polymerized unit (B) in the copolymer preferably give a mole ratio (A/B) of 5/95 to 95/5. The mole ratio is more preferably 25/75 to 95/5, still more preferably 50/50 to 95/5, because a higher proportion of the polymerized unit (A) can lead to higher hydrophilicity, resulting in less adhesion. The mole ratio is particularly preferably 60/40 to 90/10 because too high a proportion of the polymerized unit (A) may make the copolymer soluble in water, resulting in poor handleability.

The polymerized unit (A) and the polymerized unit (B) may bond in any orientations, and may be either in the head-to-head structure or in the head-to-tail structure. In other words, they may be either in the —CH$_2$—CH(OH)—CH$_2$—CX$_2$— structure or in the —CH$_2$—CH(OH)—CX$_2$—CH$_2$— structure.

The copolymer may further contain, as the polymerized units (B), a polymerized unit (B1) that is a polymerized unit (B1a), a polymerized unit (B1b), or a polymerized unit (B1c) and a polymerized unit (B2) that is a polymerized unit (B2a), polymerized unit (B2b), or a polymerized unit (B2c), each described below.

The copolymer also preferably contains, as the polymerized units (B), a polymerized unit (B1a) represented by —CH$_2$—CX$^1$$_2$— (wherein X$^1$s are the same as or different from each other, and are each H or a C3-C18 linear or branched alkoxy group optionally containing an oxygen atom or a cyclic structure between carbon atoms, excluding those in which both X$^1$s are H) and a polymerized unit (B2a) represented by —CH$_2$—CX$^2$$_2$— (wherein X$^2$s are the same as or different from each other, and are each H or an alkoxy group having a carbon number of 4 or greater, having a linear, branched, or cyclic structure, and optionally containing a hetero atom between carbon atoms, excluding those in which both X$^2$ are H).

The polymerized unit (B1a) may be —CH$_2$—CHX$^1$—.
The polymerized unit (B2a) may be —CH$_2$—CHX$^2$—.
The carbon number of the alkoxy group for X$^1$ is preferably 4 to 12.

$X^1$ is preferably a group represented by the formula: —O—Z (wherein Z is a C4-C18 linear alkyl group, a C4-C9 branched alkyl group, a C5-C10 alkyl group having a cyclic structure, or a group represented by the formula (A): —(CH$_2$—O)$_m$—R$^4$ (wherein R$^4$ is a C1-C2 alkyl group, and m is an integer of 1 to 5)).

Specific examples of Z include groups mentioned as examples of the C4-C18 linear alkyl group, the C4-C9 branched alkyl group, the C5-C10 alkyl group having a cyclic structure, and the group represented by the formula (A): —(CH$_2$—O)$_m$—R$^4$ (wherein R$^4$ is a C1-C2 alkyl group, and m is an integer of 1 to 5) for the above Y.

The carbon number of the alkoxy group for $X^2$ is preferably 4 to 25.

$X^2$ is preferably a group represented by the formula: —O—CR$^1$R$^2$R$^3$ (wherein R$^1$, R$^2$, and R$^3$ are the same as or different from each other, and are each a C1-C8 alkyl group), a C4-C12 alkoxy group containing a hetero atom and optionally having a cyclic structure, or a C7-C18 alkoxy group optionally containing an aromatic ring.

$X^2$ is preferably a group represented by —O—CR$^1$R$^2$R$^3$ (wherein R$^1$, R$^2$, and R$^3$ are the same as or different from each other, and are each a C1-C8 alkyl group). Specifically, preferred is —O—C(Me)$_3$, —O—C(Et)$_2$(Me), or —O—C(Et)$_3$, more preferred is —O—C(Me)$_3$.

$X^2$ is also preferably a C4-C12 alkoxy group containing a hetero atom and optionally having a cyclic structure. Specifically, preferred is a group represented by the following formula.

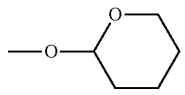

[Chem. 18]

$X^2$ is also preferably a C7-C19 alkoxy group optionally containing an aromatic ring, more preferably a C7-C18 alkoxy group. Specifically, preferred is —O—CH$_2$-Ph, —O—C(Ph)$_3$, or a group represented by the following formula:

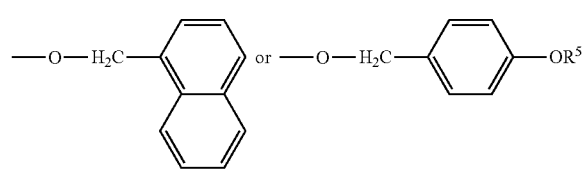

[Chem. 19]

wherein R$^5$ is Me or Et.

The copolymer also preferably contains, as the polymerized units (B),
a polymerized unit (B1b) represented by —CH$_2$—CX$^3$$_2$— (wherein X$^3$s are the same as or different from each other, and are each H or a C3-C18 linear or branched alkoxy group optionally containing an oxygen atom or a cyclic structure between carbon atoms, excluding those in which both X$^3$s are H), and
a polymerized unit (B2b) represented by —CH$_2$—CX$^4$$_2$— (wherein X$^4$s are the same as or different from each other, and are each H or a linear or branched siloxy group having a carbon number of 3 or greater, excluding those in which both X$^4$s are H).

The polymerized unit (B1b) may be —CH$_2$—CHX$^3$—.
The polymerized unit (B2b) may be —CH$_2$—CHX$^4$—.
The carbon number of the alkoxy group for $X^3$ is preferably 4 to 12.

$X^3$ is preferably a group represented by the formula: —O—Z (wherein Z is a C4-C18 linear alkyl group, a C4-C9 branched alkyl group, a C5-C10 alkyl group having a cyclic structure, or a group represented by the formula (A): —(CH$_2$—O)$_m$—R$^4$ (wherein R$^4$ is a C1-C2 alkyl group, and m is an integer of 1 to 5)).

Specific examples of Z include groups mentioned as examples of the C4-C18 linear alkyl group, the C4-C9 branched alkyl group, the C5-C10 alkyl group having a cyclic structure, and the group represented by the formula (A): —(CH$_2$—O)$_m$—R$^4$ (wherein R$^4$ is a C1-C2 alkyl group, and m is an integer of 1 to 5) for the above Y.

In the polymerized unit (B2b), $X^4$ is preferably —O—SiR$^1$R$^2$R$^3$ (wherein R$^1$, R$^2$, and R$^3$ are each a C1-C8 alkyl group or a phenyl group).

Specifically, preferred is at least one selected from the group consisting of —O—Si(Me)$_3$, —O—Si(Et)$_3$, —O—Si(Me)$_2$(tBu), —O—Si(iPr)$_3$, and —O—Si(Ph)$_2$(tBu), more preferred is at least one selected from the group consisting of —O—Si(Me)$_3$ and —O—Si(Et)$_3$.

The copolymer also preferably contains, as the polymerized units (B),
a polymerized unit (B1c) represented by —CH$_2$—CX$^5$$_2$— (wherein X$^5$s are the same as or different from each other, and are each H or an alkyl group represented by —(CH$_2$)$_n$CH$_3$ (wherein n is an integer of 0 to 16), excluding those in which both X$^5$s are H), and
a polymerized unit (B2c) represented by —CH$_2$—CX$^6$$_2$— (wherein X$^6$s are the same as or different from each other, and are each H or an ester group represented by —O(C=O)R (wherein R is a C1-C17 hydrocarbon group), excluding those in which both X$^6$s are H).

The polymerized unit (B1c) may be —CH$_2$—CHX$^5$—.
The polymerized unit (B2c) may be —CH$_2$—CHX$^6$—.
The carbon number of the alkyl group for $X^5$ is preferably 1 to 17.

$X^5$ is particularly —(CH$_2$)$_n$CH$_3$ (wherein n is an integer of 0 to 16), and n is more preferably 0 to 10, still more preferably 0 to 8, particularly preferably 0 to 6. The lower limit of n may be 2 or may be 3.

Specific examples of the group represented by —(CH$_2$)$_n$CH$_3$ (wherein n is an integer of 0 to 16) include —CH$_3$, —CH$_2$CH$_3$, —(CH$_2$)$_2$CH$_3$, —(CH$_2$)$_3$CH$_3$, and —(CH$_2$)$_4$CH$_3$.

In the polymerized unit (B2c), $X^6$ is preferably an ester group represented by —O(C=O)R (wherein R is a C1-C17 hydrocarbon group). Specifically, more preferred is at least one selected from the group consisting of —O(C=O)CH$_3$, —O(C=O)CH$_2$CH$_3$, and —O(C=O) Ph.

For the copolymer containing the polymerized unit (B1) and the polymerized unit (B2) as the polymerized units (B), the polymerized unit (B1) and the polymerized unit (B2) preferably give a mole ratio (B1/B2) of 1/99 to 99/1, more preferably 50/50 to 99/1, still more preferably 75/25 to 99/1.

The copolymer preferably has a weight average molecular weight of 1000 to 2000000, more preferably 3000 to 1000000, still more preferably 5000 to 500000. The weight average molecular weight can be determined by gel permeation chromatography (GPC).

The copolymer preferably has a molecular weight distribution (Mw/Mn) of 1 to 5, more preferably 1 to 4, still more preferably 1 to 3.5. The molecular weight distribution can be determined by gel permeation chromatography (GPC).

The copolymer can be produced by any known method.

The copolymer containing the polymerized units (B1) and (B2) as the polymerized units (B) may be produced by a method including deprotecting the copolymer containing the polymerized unit (B1) and the polymerized unit (B2), for example.

The deprotection can be performed by any known method. A deprotection reaction converts the leaving groups or hydrolyzable groups such as the alkoxy groups (e.g., a t-butoxy group), siloxy groups, or ester groups of the polymerized unit (B1) or (B2) into hydroxy groups, generating a polymerized unit (A). In this process, adjusting the degree of deprotection enables control of the mole ratio (B1/B2) of the polymerized unit (B1) and the polymerized unit (B2).

The article can reduce adhesion of proteins, blood components, cells, or bacteria, and thus can suitably be used as an antimicrobial article, a cell culture article, an antithrombotic article, or a biopharmaceutical article that needs to avoid adhesion of proteins, blood components, cells, or bacteria.

The article may be in any form, such as a film, sheet, tube, bag, petri dish, dish, well, or vial.

Examples of the proteins include plasma proteins and biopharmaceuticals to be described later. Examples of the plasma proteins include albumins, globulins, and fibrinogens. Examples of the blood components include platelets.

The antithrombotic article is preferably a vial, an artificial blood vessel, a stent, a catheter, an artificial heart, an artificial lung, an artificial heart valve, a blood bag, or the like.

Examples of the biopharmaceutical article include sheets for biopharmaceuticals, films for biopharmaceuticals, vials for biopharmaceuticals, petri dishes for biopharmaceuticals, and flasks for biopharmaceuticals.

If tools for storage of biopharmaceuticals and tools for use of biopharmaceuticals allow easy adsorption of biopharmaceuticals, they may cause a failure in quantifying or analyzing the biopharmaceuticals correctly. Such a disadvantage also causes a heavy economic loss because biopharmaceuticals are expensive. Bags for biopharmaceuticals, sheets for biopharmaceuticals, films for biopharmaceuticals, vials for biopharmaceuticals, petri dishes for biopharmaceuticals, or flasks for biopharmaceuticals formed from the aforementioned copolymer cause less adsorption of biopharmaceuticals, resulting in high-rate recovery of biopharmaceuticals.

Examples of the biopharmaceuticals include protein pharmaceuticals, recombinant viruses, cellular therapeutic agents, and nucleic acid pharmaceuticals.

Examples of the protein pharmaceuticals include (1) enzyme proteins: altelase, monteplase, imiglucerase, velaglucerase alfa, agalsidase alfa, agalsidase beta, laronidase, alglucosidase alfa, idursulfase, galsulfase, rasburicase, and dornase alfa, (2) blood coagulation and fibrinolysis factor proteins: octocog alfa, rurioctocog alfa, eptacog alfa (activated), nonacog alfa, turoctocog alfa, eftrenonacog alfa, and thrombomodulin alfa, (3) serum proteins: human serum albumin, (4) hormone proteins: human insulin, insulin lispro, insulin aspart, insulin glargine, insulin detemir, insulin glulisine, insulin degludec, insulin degludec/insulin aspart, somatropin, pegvisomant, mecasermin, carperitide, glucagon, follitropin alfa, follitropin beta, liraglutide, teriparatide, and metreleptin, (5) vaccine proteins: recombinant adsorbed Hepatitis B vaccine (prepared from yeast), dried cell-culture inactivated Hepatitis A vaccine, recombinant adsorbed bivalent human papillomavirus-like particle vaccine (prepared from Trichoplusiani cells), and recombinant adsorbed quadrivalent human papillomavirus-like particle vaccine (prepared from yeast), (6) interferon proteins: interferon alfa (NAMALWA), interferon alfa-2b, interferon alfa (BALL-1), interferon alfacon-1, interferon beta, interferon beta-1a, interferon beta-1b, interferon gamma-1a, peginterferon alfa-2a, and peginterferon alfa-2b, (7) erythropoietin proteins: epoetin alfa, epoetin beta, darbepoetin alfa, epoetin beta pegol, and epoetin kappa, (8) cytokine proteins: filgrastim, pegfilgrastim, lenograstim, nartograstim, celmoleukin, teceleukin, and trafermin, (9) antibody proteins: muromonab-CD3, trastuzumab, rituximab, palivizumab, infliximab, basiliximab, tocilizumab, gemtuzumab ozogamicin, bevacizumab, ibritumomab tiuxetan, adalimumab, cetuximab, ranibizumab, omalizumab, eculizumab, panitumumab, ustekinumab, golimumab, canakinumab, denosumab, mogamulizumab, certolizumab pegol, ofatumumab, pertuzumab, trastuzumab emtansine, brentuximab vedotin, natalizumab, nivolumab, and alemtuzumab, and (10) fusion proteins: etanercept, abatacept, romiplostim, and aflibercept.

Examples of the nucleic acid pharmaceuticals include antisense, siRNA, decoy nucleic acids, nucleic acid aptamers, ribozymes, miRNA antisense, miRNAmimic, and CpG oligodeoxynucleotides.

Examples of the antimicrobial article include contact lenses, toiletry, kitchen sink tools, indoor units such as air conditioners, food plant equipment, sewage treatment plant equipment, outdoor structures such as buildings, drainpipes, interior parts of transport such as automobiles, trains, and airplanes, and portable terminals.

Examples of the cell culture article include bags for cell culture, sheets for cell culture, films for cell culture, vials for cell culture, petri dishes for cell culture, and flasks for cell culture.

The cell culture article may also be a culture container for embryoid body formation. The culture container for embryoid body formation preferably has two or more wells. Each well may have any shape, and preferably has a bottom with a substantially U-shaped vertical cross section and a substantially circular opening. The inner surface of the bottom preferably has a radius of curvature (R') of 1.0 mm or greater and 3.5 mm or smaller, more preferably 3.0 mm or smaller. The opening preferably has a diameter of 4.0 to 11.0 mm. Each well may have a capacity of 80 to 500 μL. The culture container for embryoid body formation is preferably such that at least the inner surface of each well is formed from the copolymer.

If tools used for culturing cells allow easy adhesion of cells, they may cause reduced recovery of cultured cells, a failure in recovering the cells in the proliferated state, or qualitative change of the cells. Bags for cell culture, sheets for cell culture, films for cell culture, vials for cell culture, petri dishes for cell culture, or flasks for cell culture formed from the aforementioned copolymer cause less adhesion of cells, resulting in high recovery of the cells obtained by culturing with preferred shapes and properties of the cells.

Examples of the cells include biological cells such as stem cells, including hematopoietic stem cells, neural stem cells, mesenchymal stem cells, mesodermal stem cells, hepatic stem cells, pancreatic stem cells, and embryonic stem cells, cells obtained by differentiating stem cells into target cells, immune cells, hematopoietic cells, neural cells, vascular endothelial cells, fibroblasts, epithelial cells, keratinocytes, corneal cells, osteoblasts, chondrocytes, adipocytes, epidermal cells, hepatic cells, pancreatic β cells, cardiocytes, myelocytes, amniocytes, and cord blood cells; established cell lines such as NIH3T3 cells, 3T3-L1 cells, 3T3-E1 cells, HeLa cells, PC-12 cells, P19 cells, CHO cells (Chinese hamster oocytes), COS cells, HEK cells, Hep-G2 cells, L929 cells, C2C12 cells, Daudi cells, Jurkat cells, KG-1a cells, CTLL-2 cells, NS-1 cells, MOLT-4 cells, HUT78 cells, and MT-4 cells; a variety of hybridoma cell strains which are antibody-producing cells; and cells obtained by genetically modifying these cells.

In particular, even in cases of culturing adhesive cells which are cells easily adhering to polymer materials, the cell culture article can reduce adhesion of cultured cells.

Examples of the cells also include embryoid bodies (EB) such as embryonic stem cells (ES cells) and induced pluripotent stem cells (iPS cells).

The embryoid body formation is a technique effective in inducing differentiation of pluripotent stem cells such as ES cells in vitro, and is therefore widely used. What is important in the embryoid body formation is to culture ES cells or iPS cells in a suspended state where the cells are not in contact with the culturing container. Thus, in adhesion culturing using a common culturing container, embryoid bodies are less likely to be formed. The culturing container for embryoid body formation formed from the aforementioned copolymer enables uniform, efficient formation of high quality embryoid bodies.

In a preferred embodiment, the invention relates to the use of the article for preventing adhesion of proteins, blood components, cells, or bacteria, the article containing a copolymer that contains:

a polymerized unit (A) represented by —$CH_2$—CHOH—; and a polymerized unit (B) represented by —$CH_2$—$CX_2$—, wherein Xs are the same as or different from each other, and are each a linear or branched alkyl group having a carbon number of 2 or greater and optionally containing an oxygen atom between carbon atoms, a linear or branched alkoxy group having a carbon number of 2 or greater and optionally containing an oxygen atom between carbon atoms, or H, excluding those in which both Xs are H.

The article may be formed by molding the copolymer by any known molding method, or may be formed by applying the copolymer or a coating composition containing the copolymer to the article. The article may include a coating film formed from a coating composition that contains the copolymer, or may include the coating film on the surface of the article.

Examples of the molding method include injection molding, rotational molding, rotational lining, thermally induced phase separation, and nonsolvent induced phase separation.

The coating film means a film formed by applying the copolymer or a coating composition containing the copolymer. Examples of methods for forming the coating film include spin coating, drop casting, dip-nip coating, spray coating, brush coating, dip coating, electrostatic coating, and inkjet printing. From the viewpoint of easiness, preferred are spin coating, drop casting, and dip coating.

The coating film preferably has a thickness of 0.1 to 50 μm, more preferably 0.5 to 30 μm, still more preferably 1.0 to 20 μm.

The coating composition may contain the copolymer and an organic solvent. The coating film is preferably formed by applying the coating composition.

The organic solvent used may be hexane, methyl isobutyl ketone, ethyl acetate, butyl acetate, methanol, ethanol, 2-propanol, 2-butanol, 1-butanol, 1-hexanol, acetone, tetrahydrofuran, methyl ethyl ketone, dimethyl acetamide, dimethyl formamide, dimethyl sulfoxide, or the like. In order to easily give a transparent, uniform coating film, preferred among these are 2-butanol, 1-butanol, 1-hexanol, and tetrahydrofuran. From the viewpoint of the solubility of the copolymer, preferred are methanol, ethanol, 2-propanol, tetrahydrofuran, dimethyl acetamide, dimethyl formamide, and dimethyl sulfoxide.

The invention also relates to a copolymer containing a polymerized unit (A) represented by —$CH_2$—CHOH— and a polymerized unit (B-1) represented by —$CH_2$—$CX^7_2$—, wherein $X^7$s are the same as or different from each other, and are each an alkyl group having a carbon number of 1 or greater, having a linear, branched, or cyclic structure, and optionally containing an oxygen atom between carbon atoms. The copolymer in which both $X^7$s are alkyl groups has excellent film strength and heat resistance.

The polymerized unit (A) is a polymerized unit represented by —$CH_2$—CHOH— and based on vinyl alcohol.

The polymerized unit (B-1) is represented by —$CH_2$—$CX^7_2$—, wherein $X^7$s are the same as or different from each other, and are each an alkyl group having a carbon number of 1 or greater, having a linear, branched, or cyclic structure, and optionally containing an oxygen atom between carbon atoms.

The alkyl group is preferably free from a fluorine atom.

In order to further reduce the adhesion of proteins, blood components, cells, or bacteria, the alkyl group preferably has a carbon number of 1 to 17, more preferably 3 to 14.

The carbon number is preferably 3 or greater, and also preferably 4 or greater.

The carbon number is preferably 14 or smaller, may be 11 or smaller, and may be 9 or smaller.

Preferred specific examples of the alkyl group include —$CH_3$, —$CH_2CH_3$, —$CH_2CH_2CH_3$, and —$CH_2CH_2CH_2CH_3$.

In order to further reduce the adhesion of proteins, blood components, cells, or bacteria, the polymerized unit (A) and the polymerized unit (B-1) in the copolymer preferably give a mole ratio (A/B-1) of 5/95 to 95/5. The mole ratio is more preferably 25/75 to 95/5, still more preferably 50/50 to 95/5, because a higher proportion of the polymerized unit (A) can lead to higher hydrophilicity, resulting in less adhesion. The mole ratio is particularly preferably 60/40 to 90/10 because too high a proportion of the polymerized unit (A) may make the copolymer soluble in water, resulting in poor handleability.

The polymerized unit (A) and the polymerized unit (B-1) may bond in any orientations, and may be either in the head-to-head structure or in the head-to-tail structure. In other words, they may be either in the —$CH_2$—CH(OH)—$CH_2$—$CX_2$— structure or in the —$CH_2$—CH(OH)—$CX_2$—$CH_2$— structure.

The copolymer preferably has a weight average molecular weight of 1000 to 2000000, more preferably 3000 to 1000000, still more preferably 5000 to 500000. The weight average molecular weight can be determined by gel permeation chromatography (GPC).

The copolymer preferably has a molecular weight distribution (Mw/Mn) of 1 to 5, more preferably 1 to 4, still more preferably 1 to 3.5. The molecular weight distribution can be determined by gel permeation chromatography (GPC).

The copolymer can be produced by any known method. For example, the copolymer may be produced by polymerizing a branched alkene such as 2-methyl-1-pentene and vinyl acetate to form a branched alkene/vinyl acetate copolymer, and then saponifying the resulting branched alkene/vinyl acetate copolymer. The polymerization and the saponification may be performed under conditions that enable formation of a desired copolymer, without any special conditions.

The copolymer can reduce adhesion of proteins, blood components, cells, or bacteria, and thus can suitably be used as a material of an antimicrobial article, a cell culture article, an antithrombotic article, or a biopharmaceutical article that needs to avoid adhesion of proteins, blood components, cells, or bacteria.

EXAMPLES

The invention is described with reference to examples, but the invention is not intended to be limited by these examples.

The parameters in the examples were determined by the following methods.

[Calculation of VOH Composition by Nuclear Magnetic Resonance (NMR)]

1H-NMR measurement condition: 400 MHz (tetramethylsilane=0 ppm)

[Molecular Weight and Molecular Weight Distribution]

The average molecular weight was calculated from the data determined by gel permeation chromatography (GPC) with a flow of tetrahydrofuran (THF) as a solvent at a flow rate of 1 ml/min. The detector and the calibration curve sample used were RI and a polystyrene standard sample. The measurement was performed at a flow rate of 1 ml/min and a sample charge amount of 200 μL.

Alternatively, the average molecular weight was calculated from the data determined by gel permeation chromatography (GPC) with a flow of dimethyl formamide (DMF) as a solvent at a flow rate of 1 ml/min. The detector and the calibration curve sample used were RI and a polymethyl methacrylate standard sample. The measurement was performed at a flow rate of 1 ml/min and a sample charge amount of 100 μL.

[Measurement of Degree of Saponification of Vinyl Acetate Unit by IR Analysis]

The degree of saponification was determined at room temperature using a Fourier transform infrared spectrophotometer.

Synthesis Example 1

Synthesis of 1-Hexene/Vinyl Alcohol (28/72 (Mol %)) Copolymer (1)

1. Synthesis of 1-Hexene/Vinyl Acetate Copolymer

An argon-purged reaction container was charged with 37.6 mL methanol, 2.78 g 1-hexene, 6.64 g vinyl acetate, and 1.23 g azobisisobutyronitrile (AIBN), and the components were reacted at 60° C. for 24 hours. The resulting polymer had a weight average molecular weight of 12800 and a molecular weight distribution of 1.58. 1H-NMR measurement showed that the composition ratio by mole of 1-hexene and vinyl acetate in the polymer was 15/85.

2. Saponification of 1-Hexene/Vinyl Acetate Copolymer

A 10 wt % methanol solution of the polymer obtained above was mixed with a 5 wt % methanol solution of sodium hydroxide such that the sodium hydroxide was in an amount of 0.13 equivalents relative to the vinyl acetate unit, and the mixture was treated at room temperature. IR was performed to confirm disappearance of the acetyl groups. The mixture was then neutralized with hydrochloric acid and purified. Thereby, a 1-hexene/vinyl alcohol copolymer (1) was obtained. The resulting polymer had a weight average molecular weight of 8600 and a molecular weight distribution of 2.52. 1H-NMR measurement showed that the composition ratio by mole of 1-hexene and vinyl alcohol in the polymer was 28/72.

Example 1

A 0.1% by mass methanol solution of the copolymer (1) was spin-coated on one reaction surface of a PET-coated QCM chip (disc shape, diameter: 1.4 cm) at room temperature. Specifically, 30 μL of the solution was dropped onto the PET-coated QCM chip and the workpiece was rotated at 2000 rpm for 60 seconds. The workpiece was then dried under reduced pressure using a rotary vacuum pump at room temperature for three hours. Thereby, a coating film (QCM chip) was obtained. The resulting coating film was incorporated into QCM-D, and the protein adsorption test (bovine serum albumin) on the coating film was performed by the following method for evaluation. The experimental results are shown in Table 1.

[Protein Adsorption Test]

The QCM chip prepared by stacking the copolymer (1) on the PET-coated QCM chip by the above method was mounted on QCM-D, and the workpiece was stabilized in phosphate-buffered saline (PBS) in a 23.4° C. environment.

The horizontality of the frequency baseline was confirmed, and then 0.5 mL phosphate-buffered saline containing proteins (concentration of proteins: 0.05 mg/mL) was injected into the system. The variation in frequency during 30-minute adsorption was measured. The proteins used were bovine serum albumin (BSA) or bovine plasma fibrinogen (BPF) and immunoglobulin G (IgG) from bovine serum.

The amount of the proteins adsorbed on the coating film was calculated by analyzing the frequency after 30-minute adsorption obtained by the experiment with regard to the areal mass (ng/cm$^2$) using the Sauerbrey equation in analysis software QTools.

Examples 2 and 3

Adsorption of bovine plasma fibrinogen (BPF) and globulin (IgG) on the copolymer (1) was evaluated as in Example 1 using QCM-D, as shown in Tables 2 and 3. The experimental results are shown in Tables 2 and 3.

Comparative Examples 1 to 3 (PET)

A 1.0% by mass solution of polyethylene terephthalate (PET) (dissolved in a solvent mixture of trifluoroacetic acid, dichloromethane, and 1,1,2,2-tetrachloroethane (mixing ratio: 1/4/45)) was spin-coated on one reaction surface of a QCM chip (disc shape, diameter: 1.4 cm) at room temperature. Specifically, 30 μL of the solution was dropped onto the QCM chip and the workpiece was rotated at 2000 rpm for 60 seconds. The workpiece was then dried under reduced pressure using a rotary vacuum pump at 50° C. for three hours or longer. Thereby, a coating film was obtained.

The resulting coating films were subjected to the protein adsorption test as in Examples 1 to 3. The experimental results are shown in Tables 1 to 3.

TABLE 1

| Albumin adsorption | Copolymer | Amount of proteins adsorbed (BSA) Value of Comparative Example 1 taken as 100 |
|---|---|---|
| Example 1 | (1) | −2.4 ± 2.0 |
| Comparative Example 1 | PET | 100 |

TABLE 2

| Fibrinogen adsorption | Copolymer | Amount of proteins adsorbed (BPF) Value of Comparative Example 2 taken as 100 |
|---|---|---|
| Example 2 | (1) | 0.6 ± 0.5 |
| Comparative Example 2 | PET | 100 |

TABLE 3

| Globulin adsorption | Copolymer | Amount of proteins adsorbed (IgG) Value of Comparative Example 3 taken as 100 |
|---|---|---|
| Example 3 | (1) | −8.3 ± 13 |
| Comparative Example 3 | PET | 100 |

Synthesis Example 2

Synthesis of 1-Hexene/Vinyl Alcohol (22/78 (Mol %)) Copolymer (2)

1. Synthesis of 1-Hexene/Vinyl Acetate Copolymer

A copolymer was obtained as in Synthesis Example 1, except that no solvent was used, 0.312 g AIBN was used, and the reaction duration was 48 hours. 1H-NMR measurement showed that the composition ratio by mole of 1-hexene and vinyl acetate in the polymer was 19/81.

2. Saponification of 1-Hexene/Vinyl Acetate Copolymer

A 10 wt % methanol solution of the polymer obtained above was mixed with a 5 wt % methanol solution of sodium hydroxide such that the sodium hydroxide was in an amount of 0.13 equivalents relative to the vinyl acetate unit, and the mixture was treated at room temperature. IR was performed to confirm disappearance of the acetyl groups. The mixture was then neutralized with hydrochloric acid and purified. Thereby, a 1-hexene/vinyl alcohol copolymer (2) was obtained. The resulting polymer had a weight average molecular weight of 10700 and a molecular weight distribution of 2.54. 1H-NMR measurement showed that the composition ratio by mole of 1-hexene and vinyl alcohol in the polymer was 22/78.

Synthesis Example 3

Synthesis of 1-Hexene/Vinyl Alcohol (10/90 (Mol %)) Copolymer (3)

1. Synthesis of 1-Hexene/Vinyl Acetate Copolymer

A copolymer was obtained as in Synthesis Example 1, except that no solvent was used, 8.19 g vinyl acetate, 3.42 g 1-hexene, and 0.0312 g AIBN were used, and the reaction duration was 30 hours. The resulting polymer had a weight average molecular weight of 40000 and a molecular weight distribution of 1.79. 1H-NMR measurement showed that the composition ratio by mole of 1-hexene and vinyl acetate in the polymer was 9/91.

2. Saponification of 1-Hexene/Vinyl Acetate Copolymer

A 10 wt % methanol solution of the polymer obtained above was mixed with a 5 wt % methanol solution of sodium hydroxide such that the sodium hydroxide was in an amount of 0.13 equivalents relative to the vinyl acetate unit, and the mixture was treated at room temperature. IR was performed to confirm disappearance of the acetyl groups. The mixture was then neutralized with hydrochloric acid and purified. Thereby, a 1-hexene/vinyl alcohol copolymer (3) was obtained. 1H-NMR measurement showed that the composition ratio by mole of 1-hexene and vinyl alcohol in the polymer was 10/90.

Synthesis Example 4

Synthesis of 2-Methyl-1-Pentene/Vinyl Alcohol (29/71 (Mol %)) Copolymer (4)

1. Copolymerization of 2-Methyl-1-Pentene/Vinyl Acetate

An argon-purged reaction container was charged with 0.54 mL anisole, 4.62 g 2-methyl-1-pentene, 4.74 g vinyl acetate, and 1.23 g azobisisobutyronitrile (AIBN), and the components were reacted at 60° C. for 48 hours. The resulting polymer had a weight average molecular weight of 6800 and a molecular weight distribution of 1.61. 1H-NMR showed that the composition ratio by mole of 2-methyl-1-pentene and vinyl acetate in the polymer was 22/78.

2. Saponification of 2-Methyl-1-Pentene/Vinyl Acetate Copolymer

A 10 wt % methanol solution of the polymer obtained above was mixed with a 5 wt % methanol solution of sodium hydroxide such that the sodium hydroxide was in an amount of 0.13 equivalents relative to the vinyl acetate unit, and the mixture was treated at room temperature for seven days. IR was performed to confirm disappearance of the acetyl groups. The mixture was then neutralized with hydrochloric acid and purified. Thereby, a 1-hexene/vinyl alcohol copolymer (4) was obtained. The resulting polymer had a weight average molecular weight of 6400 and a molecular weight distribution of 2.54. 1H-NMR measurement showed that the degree of saponification was 88.4% and that the composition ratio of 2-methyl-1-pentene and vinyl alcohol in the polymer was 29/71.

Synthesis Example 5

Synthesis of 2-Methyl-1-Pentene/Vinyl Alcohol (20/80 (Mol %)) Copolymer (5)

1. Copolymerization of 2-Methyl-1-Pentene/Vinyl Acetate

A copolymer was obtained as in Synthesis Example 4, except that 2.78 g 2-methyl-1-pentene and 6.64 g vinyl acetate were used. The resulting polymer had a weight average molecular weight of 15200 and a molecular weight distribution of 4.57. 1H-NMR showed that the composition ratio by mole of 2-methyl-1-pentene and vinyl acetate in the polymer was 16/84.

2. Saponification of 2-Methyl-1-Pentene/Vinyl Acetate Copolymer

A 10 wt % methanol solution of the polymer obtained above was mixed with a 5 wt % methanol solution of sodium hydroxide such that the sodium hydroxide was in an amount of 0.13 equivalents relative to the vinyl acetate unit, and the mixture was treated at room temperature for seven days. IR was performed to confirm disappearance of the acetyl groups. The mixture was then neutralized with hydrochloric acid and purified. Thereby, a 1-hexene/vinyl alcohol copolymer (5) was obtained. The resulting polymer had a weight average molecular weight of 7800 and a molecular weight distribution of 2.61. 1H-NMR measurement showed that the degree of saponification was 92.9% and that the composition ratio of 2-methyl-1-pentene and vinyl alcohol in the polymer was 20/80.

Synthesis Example 6

Synthesis of 2-Methyl-1-Pentene/Vinyl Alcohol (11/89 (Mol %)) Copolymer (6)

1. Copolymerization of 2-Methyl-1-Pentene/Vinyl Acetate

A copolymer was obtained as in Synthesis Example 4, except that 0.926 g 2-methyl-1-pentene and 8.33 g vinyl acetate were used and the reaction duration was 24 hours. The resulting polymer had a weight average molecular weight of 53100 and a molecular weight distribution of 2.69. 1H-NMR showed that the composition ratio by mole of 2-methyl-1-pentene and vinyl acetate in the polymer was 8/92.

2. Saponification of 2-Methyl-1-Pentene/Vinyl Acetate Copolymer

A 10 wt % methanol solution of the polymer obtained above was mixed with a 5 wt % methanol solution of sodium hydroxide such that the sodium hydroxide was in an amount of 0.13 equivalents relative to the vinyl acetate unit, and the mixture was treated at room temperature for seven days. IR was performed to confirm disappearance of the acetyl groups. The mixture was then neutralized with hydrochloric acid and purified. Thereby, a 1-hexene/vinyl alcohol copolymer (6) was obtained. 1H-NMR measurement showed that the degree of saponification was 94.7% and that the composition ratio of 2-methyl-1-pentene and vinyl alcohol in the polymer was 11/89.

Examples 4 to 16

Coating films were obtained using the copolymers (2) to (6) as in Examples 1 to 3. The protein adsorption test (adsorption of bovine serum albumin (BSA), bovine plasma fibrinogen (BPF), and globulin (IgG)) on the coating films was performed for evaluation. The experimental results are shown in Tables 4 to 16.

Comparative Examples 4 to 16 (PET)

Coating films were obtained as in Comparative Example 1.

The resulting coating films were subjected to the protein adsorption test as in Examples 4 to 16. The experimental results are shown in Tables 4 to 16.

Example 17

The copolymer (2) was spin-coated onto a PET film (1.0 cm×1.0 cm) to prepare a coating film, and this coating film was fixed on the bottom of a 24-well cell-culture plate with a small amount of silicone adhesive. The workpiece was washed with ultrapure water three times, and then immersed in PBS in a 37° C. environment for 12 hours. The resulting coating film was subjected to a cell adhesion test (NIH3T3 cells) on the coating film by the following method for evaluation.

[Cell Adhesion Test]

Mouse fibroblasts (NIH3T3) were cultured in a Dulbecco's modified Eagle medium containing 10% fetal calf serum (FCS) (FCS-containing DMEM) in an environment of 5% $CO_2$ and 37° C. The cultured NIH3T3 cells were washed with sterilized PBS once, and then mixed with 1 mL of a 0.02% ethylenediaminetetraacetic acid (EDTA) solution and 1 mL of a 0.25% trypsin solution. The culture was peeled off the cell-culture plate. A suspension of the cells was centrifuged and the NIH3T3 cells were collected. The cells were again suspended in FCS-containing DMEM, whereby a solution of $61.2 \times 10^4$ cells/mL was obtained.

The cell suspension was prepared on a medium at $2 \times 10^4$ cells/cm$^2$ for each well of the cell-culture plate with the coating film fixed thereon, and the cells were seeded on the coating film. The cells were cultured in an environment of 5% $CO_2$ and 37° C. for one hour. The coating film was then washed with PBS three times and mixed with 400 μL/well of a 1000-fold dilution of calcein-AM solution. The cells were then cultured in an environment of 5% $CO_2$ and 37° C. for 20 minutes. Any three visual fields of each coating film were observed using a fluorescent microscope, and the number of adhesion cells was counted. The experimental results are shown in Table 17.

Examples 18 and 19

Coating films were obtained as in Example 17, except that the copolymers (4) and (5) were used. The cell adhesion test (NIH3T3 cells) on the coating films was performed for evaluation.

Comparative Examples 17 to 19 (PET)

A 1.0% by mass solution of polyethylene terephthalate (PET) (dissolved in a solvent mixture of trifluoroacetic acid, dichloromethane, and 1,1,2,2-tetrachloroethane (mixing ratio: 1/4/45)) was spin-coated on one reaction surface of a QCM chip (disc shape, diameter: 1.4 cm) at room temperature. Specifically, 30 μL of the solution was dropped onto the QCM chip, and the workpiece was rotated at 2000 rpm for 60 seconds. The workpiece was then dried under reduced pressure using a rotary vacuum pump at 50° C. for three hours or longer. Thereby, a coating film was obtained.

The resulting coating films were subjected to the cell adhesion test as in Examples 17 to 19. The experimental results are shown in Tables 17 to 19.

TABLE 4

| Albumin adsorption | Copolymer | Amount of proteins adsorbed (BSA) Value of Comparative Example 4 taken as 100 |
|---|---|---|
| Example 4 | (2) | 2.17 ± 1.78 |
| Comparative Example 4 | PET | 100 |

TABLE 5

| Fibrinogen adsorption | Copolymer | Amount of proteins adsorbed (BPF) Value of Comparative Example 5 taken as 100 |
|---|---|---|
| Example 5 | (2) | 0.686 ± 0.435 |
| Comparative Example 5 | PET | 100 |

TABLE 6

| Globulin adsorption | Copolymer | Amount of proteins adsorbed (IgG) Value of Comparative Example 6 taken as 100 |
|---|---|---|
| Example 6 | (2) | 1.31 ± 0.727 |
| Comparative Example 6 | PET | 100 |

TABLE 7

| Albumin adsorption | Copolymer | Amount of proteins adsorbed (BSA) Value of Comparative Example 7 taken as 100 |
|---|---|---|
| Example 7 | (3) | 0.91 ± 0.96 |
| Comparative Example 7 | PET | 100 |

TABLE 8

| Fibrinogen adsorption | Copolymer | Amount of proteins adsorbed (BPF) Value of Comparative Example 8 taken as 100 |
|---|---|---|
| Example 8 | (3) | 0.67 ± 0.41 |
| Comparative Example 8 | PET | 100 |

TABLE 9

| Globulin adsorption | Copolymer | Amount of proteins adsorbed (IgG) Value of Comparative Example 9 taken as 100 |
|---|---|---|
| Example 9 | (3) | 1.0 ± 0.55 |
| Comparative Example 9 | PET | 100 |

TABLE 10

| Albumin adsorption | Copolymer | Amount of proteins adsorbed (BSA) Value of Comparative Example 10 taken as 100 |
|---|---|---|
| Example 10 | (4) | 10.2 ± 3.16 |
| Comparative Example 10 | PET | 100 |

TABLE 11

| Fibrinogen adsorption | Copolymer | Amount of proteins adsorbed (BPF) Value of Comparative Example 11 taken as 100 |
|---|---|---|
| Example 11 | (4) | 2.43 ± 0.616 |
| Comparative Example 11 | PET | 100 |

TABLE 12

| Globulin adsorption | Copolymer | Amount of proteins adsorbed (IgG) Value of Comparative Example 12 taken as 100 |
|---|---|---|
| Example 12 | (4) | 3.15 ± 1.11 |
| Comparative Example 12 | PET | 100 |

TABLE 13

| Albumin adsorption | Copolymer | Amount of proteins adsorbed (BSA) Value of Comparative Example 13 taken as 100 |
|---|---|---|
| Example 13 | (5) | 2.33 ± 0.340 |
| Comparative Example 13 | PET | 100 |

TABLE 14

| Fibrinogen adsorption | Copolymer | Amount of proteins adsorbed (BPF) Value of Comparative Example 14 taken as 100 |
|---|---|---|
| Example 14 | (5) | 3.04 ± 2.40 |
| Comparative Example 14 | PET | 100 |

TABLE 15

| Globulin adsorption | Copolymer | Amount of proteins adsorbed (IgG) Value of Comparative Example 15 taken as 100 |
|---|---|---|
| Example 15 | (5) | 1.60 ± 0.572 |
| Comparative Example 15 | PET | 100 |

TABLE 16

| Albumin adsorption | Copolymer | Amount of proteins adsorbed (BSA) Value of Comparative Example 16 taken as 100 |
|---|---|---|
| Example 16 | (6) | 31.29 |
| Comparative Example 16 | PET | 100 |

TABLE 17

| Cell adhesion | Copolymer | Amount of cells adsorbed (NIH3T3) Value of Comparative Example 17 taken as 100 |
|---|---|---|
| Example 17 | (2) | 35.6 ± 10.1 |
| Comparative Example 17 | PET | 100 |

TABLE 18

| Cell adhesion | Copolymer | Amount of cells adsorbed (NIH3T3) Value of Comparative Example 18 taken as 100 |
|---|---|---|
| Example 18 | (4) | 38.2 ± 18.9 |
| Comparative Example 18 | PET | 100 |

TABLE 19

| Cell adhesion | Copolymer | Amount of cells adsorbed (NIH3T3) Value of Comparative Example 19 taken as 100 |
|---|---|---|
| Example 19 | (5) | 18.3 ± 5.65 |
| Comparative Example 19 | PET | 100 |

The invention claimed is:

1. A cell culture article comprising a copolymer, the copolymer comprising:

a polymerized unit (A) represented by —$CH_2$—CHOH—; and a polymerized unit (B) represented by —$CH_2$—$CX_2$—, wherein Xs are the same as or different from each other, and are each selected from the group consisting of an alkyl group represented by —$(CH_2)_n CH_3$ (wherein n is an integer of 0 to 16); an ester group represented by —O(C=O)R (wherein R is a C1-C19 hydrocarbon group); or H, excluding those in which both Xs are H, wherein if one of the two Xs is H and the other X is the alkyl group, n is 2 or more, wherein if both of the two Xs are the alkyl groups, n is 0 for one of the two Xs and n is 2 or more for the other X, at least one of the two Xs is a group represented by the formula: —$(CH_2)_n CH_3$ (wherein n is an integer of 2 to 16), and wherein the copolymer is a saponified copolymer.

2. The article according to claim 1, wherein the polymerized unit (A) and the polymerized unit (B) give a mole ratio (AB) of 5/95 to 95/5.

3. A copolymer comprising:

a polymerized unit (A) represented by —$CH_2$—CHOH—; and a polymerized unit (B-1) represented by —$CH_2$—$CX_2$—, wherein Xs are the same as or different from each other, and are each an alkyl group having a carbon number of 1 or greater, having a linear, branched, or cyclic structure, and at least one of the two Xs is a group represented by the formula: —$(CH_2)_n CH_3$ (wherein n is an integer of 2 to 16), and wherein the copolymer is a saponified copolymer.

4. The cell culture article of claim 1, wherein the article is a bag, a sheet, a film, a vial, a petri dish, or a flask.

* * * * *